(12) United States Patent
Desai et al.

(10) Patent No.: US 11,932,665 B2
(45) Date of Patent: Mar. 19, 2024

(54) CYCLIC THIOL PRODRUGS

(71) Applicant: Lilac Therapeutics, Inc., Walnut Creek, CA (US)

(72) Inventors: Manoj Chandrasinhji Desai, Martinez, CA (US); Siva R. Kamma, Hyderabad (IN)

(73) Assignee: Lilac Therapeutics, Inc., Walnut Creek, CA (US)

( * ) Notice: Subject to any disclaimer, the term of this patent is extended or adjusted under 35 U.S.C. 154(b) by 0 days.

(21) Appl. No.: 18/147,178

(22) Filed: Dec. 28, 2022

(65) Prior Publication Data

US 2023/0234979 A1 Jul. 27, 2023

Related U.S. Application Data

(60) Provisional application No. 63/296,057, filed on Jan. 3, 2022.

(51) Int. Cl.
  *C07F 9/6578* (2006.01)
  *C07F 9/6584* (2006.01)

(52) U.S. Cl.
  CPC ...... *C07F 9/65848* (2013.01); *C07F 9/65785* (2013.01)

(58) Field of Classification Search
  CPC .................................. C07F 9/65785
  See application file for complete search history.

(56) References Cited

U.S. PATENT DOCUMENTS

| | | |
|---|---|---|
| 3,536,809 A | 10/1970 | Applezweig |
| 3,598,123 A | 8/1971 | Zaffaroni |
| 3,710,795 A | 1/1973 | Iguchi et al. |
| 3,845,770 A | 11/1974 | Theeuwes et al. |
| 3,916,899 A | 11/1975 | Theeuwes et al. |
| 3,932,403 A | 1/1976 | Ashton et al. |
| RE28,819 E | 5/1976 | Thompson |
| 4,008,719 A | 2/1977 | Theeuwes et al. |
| 4,044,126 A | 8/1977 | Cook et al. |
| 4,328,245 A | 5/1982 | Yu et al. |
| 4,358,603 A | 11/1982 | Yu |
| 4,364,923 A | 12/1982 | Cook et al. |
| 4,409,239 A | 10/1983 | Yu |
| 4,410,545 A | 10/1983 | Yu et al. |
| 4,414,209 A | 11/1983 | Cook et al. |
| 4,522,811 A | 6/1985 | Eppstein et al. |
| 5,033,252 A | 7/1991 | Carter |
| 5,052,558 A | 10/1991 | Carter |
| 5,059,595 A | 10/1991 | Le Grazie |
| 5,073,543 A | 12/1991 | Marshall et al. |
| 5,120,548 A | 6/1992 | McClelland et al. |
| 5,323,907 A | 6/1994 | Kalvelage |
| 5,354,556 A | 10/1994 | Sparks et al. |
| 5,512,668 A | 4/1996 | Stec et al. |
| 5,591,767 A | 1/1997 | Mohr et al. |
| 5,639,476 A | 6/1997 | Oshlack et al. |
| 5,639,480 A | 6/1997 | Bodmer et al. |
| 5,674,533 A | 10/1997 | Santus et al. |
| 5,709,874 A | 1/1998 | Hanson et al. |
| 5,733,566 A | 3/1998 | Lewis |
| 5,739,108 A | 4/1998 | Mitchell |
| 5,759,542 A | 6/1998 | Gurewich |
| 5,840,674 A | 11/1998 | Yatvin et al. |
| 5,860,957 A | 1/1999 | Jacobsen et al. |
| 5,891,474 A | 4/1999 | Busetti et al. |
| 5,900,252 A | 5/1999 | Calanchi et al. |
| 5,922,356 A | 7/1999 | Koseki et al. |
| 5,948,433 A | 9/1999 | Burton et al. |
| 5,972,366 A | 10/1999 | Haynes et al. |
| 5,972,891 A | 10/1999 | Kamei et al. |
| 5,980,945 A | 11/1999 | Ruiz |
| 5,983,134 A | 11/1999 | Ostrow |
| 5,985,307 A | 11/1999 | Hanson et al. |
| 5,985,317 A | 11/1999 | Venkateshwaran et al. |
| 5,993,855 A | 11/1999 | Yoshimoto et al. |
| 6,004,534 A | 12/1999 | Langer et al. |
| 6,010,715 A | 1/2000 | Wick et al. |
| 6,024,975 A | 2/2000 | D'Angelo et al. |
| 6,039,975 A | 3/2000 | Shah et al. |
| 6,045,830 A | 4/2000 | Igari et al. |
| 6,048,736 A | 4/2000 | Kosak |
| 6,060,082 A | 5/2000 | Chen et al. |

(Continued)

FOREIGN PATENT DOCUMENTS

| | | | | |
|---|---|---|---|---|
| GB | 1402296 A | * | 8/1975 | ............... C07F 9/24 |
| WO | 2000/13690 A1 | | 3/2000 | |
| WO | 2005/025506 A2 | | 3/2005 | |

OTHER PUBLICATIONS

Ali et al., Heteroatom Chemistry (1999), 10(6), pp. 475-480. (Year: 1999).*
Chou et al., Yaoxue Xuebao (1964), 11(9), pp. 617-625. (Year: 1964).*
Chemical Abstracts Registry No. 141931-15-9, indexed in the Registry file on Jun. 19, 1992. (Year: 1992).*
Chou et al., CA 62:5199 (1965). (Year: 1965).*
Pubchem CID 16407, Create date: Aug. 8, 2005 (Aug. 8, 2005), entire document, especially 1 p. 2, compound isted.
Okruszek e t a l., "Synthesis of Oligo(deoxyribonucleoside phosphorodithioate)s by the Dithiaphospholane Approach", Oct. 1, 1995 (Oct. 1, 1995), The Journal of Organic Chemistry, 60; 21, pp. 6998-7005, entire document, especially Schemes 1-2.

(Continued)

*Primary Examiner* — Laura L Stockton
(74) *Attorney, Agent, or Firm* — Young Basile Hanlon & MacFarlane, P.C.

(57) ABSTRACT

Disclosed herein are cyclic thiol prodrugs, and pharmaceutical compositions thereof. The prodrugs and pharmaceutical compositions thereof may be used to treat or prevent medical disorders such as, for example, cystinuria, cystinosis, cancer, neurodegenerative disease, Parkinson's disease, Huntington's disease, malaria, nonalcoholic fatty liver disease, radiation poisoning, arsenic poisoning, radioprotection, Wilson's disease or rheumatoid arthritis.

6 Claims, No Drawings

(56) References Cited

U.S. PATENT DOCUMENTS

| | | | |
|---|---|---|---|
| 6,071,495 | A | 6/2000 | Unger et al. |
| 6,087,324 | A | 7/2000 | Igari et al. |
| 6,113,943 | A | 9/2000 | Okada et al. |
| 6,120,751 | A | 9/2000 | Unger |
| 6,131,570 | A | 10/2000 | Schuster et al. |
| 6,139,865 | A | 10/2000 | Friend et al. |
| 6,167,301 | A | 12/2000 | Flower et al. |
| 6,197,350 | B1 | 3/2001 | Yamagata et al. |
| 6,248,363 | B1 | 6/2001 | Patel et al. |
| 6,253,872 | B1 | 7/2001 | Neumann |
| 6,256,533 | B1 | 7/2001 | Yuzhakov et al. |
| 6,261,595 | B1 | 7/2001 | Stanley et al. |
| 6,264,970 | B1 | 7/2001 | Hata et al. |
| 6,267,981 | B1 | 7/2001 | Okamoto et al. |
| 6,267,983 | B1 | 7/2001 | Fujii et al. |
| 6,271,359 | B1 | 8/2001 | Norris et al. |
| 6,274,552 | B1 | 8/2001 | Tamarkin et al. |
| 6,316,652 | B1 | 11/2001 | Steliou |
| 6,376,461 | B1 | 4/2002 | Igari et al. |
| 6,419,961 | B1 | 7/2002 | Igari et al. |
| 6,589,548 | B1 | 7/2003 | Oh et al. |
| 6,613,358 | B2 | 9/2003 | Randolph et al. |
| 6,699,500 | B2 | 3/2004 | Okada et al. |
| 6,740,634 | B1 | 5/2004 | Saikawa et al. |
| 2009/0213528 | A1 | 8/2009 | Ohtsuki |
| 2011/0236931 | A1 | 9/2011 | Cashman et al. |
| 2013/0216919 | A1 | 8/2013 | Tokuda et al. |

OTHER PUBLICATIONS

Besouw M, Masereeuw R, van den Heuvel L, Levtchenko E. Cysteamine: an old drug with new potential. Drug Discov Today. Aug. 2013; 18(15-16):785-92. doi: 10.1016/j.drudis.2013.02.003. Epub Feb. 14, 2013.

Brittain, H., Chapter 6, pp. 205-208 in Polymorphism in Pharmaceutical Solids, (Brittain, H. ed.), Marcel Dekker, Inc. New York, 1999.

Guillory, K., Chapter 5, pp. 202-205 in Polymorphism in Pharmaceutical Solids, (Brittain, H. ed.), Marcel Dekker, Inc., New York, NY, 1999).

Holodiag, Pharmaparc II, Voie de l'Innovation, 27 100 Val de Reuil, France; accessed Jun. 29, 2023 http://www.holodiag.com.

Jens T. Carstensen, Drug Stability: Principles & Practice, 2d. Ed., Marcel Dekker, NY, NY, 1995, pp. 379-380.

Atkuri KR, Mantovani JJ, Herzenberg LA, Herzenberg LA. N-Acetylcysteine—a safe antidote for cysteine/glutathione deficiency. Curr Opin Pharmacol. Aug. 2007;7(4):355-9. doi: 10.1016/j.coph. 2007.04.005. Epub Jun. 29, 2007.

Saudek CD, Selam JL, Pitt HA, Waxman K, Rubio M, Jeandidier N, Turner D, Fischell RE, Charles MA. A preliminary trial of the programmable implantable medication system for insulin delivery. N Engl J Med. Aug. 31, 1989;321(9):574-9.

Langer, Robert. "New methods of drug delivery." Science 249.4976 (1990): 1527-1533.

Sefton, CRC Crit. Ref. Biomed. Eng. 14:201 (1987.

F. Cicchetti, L.S. David, A. Siddu, H.L. Denis, Cysteamine as a novel disease-modifying compound for Parkinson's disease: Over a decade of research supporting a clinical trial, Neurobiology of Disease, vol. 130, 2019, 104530, ISSN 0969-9961.

Pfaff, Annalise R., et al. "Medicinal thiols: Current status and new perspectives." Mini reviews in medicinal chemistry 20.6 (2020): 513-529.

* cited by examiner

CYCLIC THIOL PRODRUGS

CROSS-REFERENCE TO RELATED APPLICATIONS

This application claims the benefit under 35 U.S.C. § 119(e) of U.S. Provisional Application No. 63/296,057, filed Jan. 3, 2022, which is hereby incorporated by reference in its entirety.

FIELD

Disclosed herein are cyclic thiol prodrugs, and pharmaceutical compositions thereof. The prodrugs and pharmaceutical compositions thereof may be used to treat or prevent medical disorders such as, for example, cystinuria, cystinosis, cancer, neurodegenerative disease, Parkinson's disease, Huntington's disease, malaria, nonalcoholic fatty liver disease, radiation poisoning, arsenic poisoning, radioprotection, Wilson's disease or rheumatoid arthritis.

BACKGROUND

Most living organisms contain high concentrations of low-molecular-weight (LMW) thiols that serve as redox buffers which protects cells against a variety of reactive chemical species, such as, for example, reactive oxygen species (ROS), reactive nitrogen species, reactive electrophilic species, metalloids, and some antibiotics. Glutathione (GSH) is the most ubiquitous of these LMW thiols, but certain cells contain high concentrations of other sulfur compounds, such as, for example, cysteine (Cys), c-glutamylcysteine (cGC), bacillithiol (BSH), mycothiol (MSH), trypanothione (TSG), ovothiol, coenzyme A (CoA) and ergothioneine (ESH). The concentrations and thiol/disulfide ratios of these different LMW thiols influence the redox potential of the reducing environment in cells that is essential for many metabolic processes.

The thiol (—SH) functional group is found in a number of drug compounds as well human metabolites and confers a unique combination of useful properties. Thiol-containing drugs can reduce radicals and other toxic electrophiles, restore cellular thiol pools, and form stable complexes with heavy metals such as lead, arsenic, and copper. Thus, thiol drugs can treat a variety of conditions by serving as radical scavengers, GSH prodrugs, or metal chelators. Many thiol drugs have been used for decades, yet continued exploration of their properties has yielded insights for the development of new treatments and optimization of clinical applications. Thiols and their conjugate bases, thiolates, are also good nucleophiles, and therefore reactive toward electrophilic species, including ROS/RNS. Thus, thiol drugs are used as ROS/RNS scavengers to prevent them from oxidizing nearby molecules, including proteins, lipids, and DNA.

A well know thiol is N-acetylcysteine (NAC) and its derivatives. In vitro and in vivo studies have shown that NAC acts as a cysteine prodrug and a GSH precursor. NAC can also reduce disulfide bonds in proteins, scavenge free radicals and bind metals to form complexes. However, the principal use pharmacologically is to replenish the cysteine and GSH that are lost due to acetaminophen toxicity. The best-known NAC formulation is Mucomyst™ (or the generic version thereof). Although commonly administered orally for the treatment of acetaminophen overdose, the formulation has a strong, disagreeable flavor and therefore is usually mixed with a fruit juice or a soft drink before consumption. Furthermore, the length of treatment required for effective use of the formulation results in longer hospital stays and higher overall healthcare expenses for oral NAC (Kondala et al., *Current Opinion in Pharmacology* 2007, 7:355-359).

Another thiol used in clinical settings is cysteamine which is an amino thiol. Endogenously, cysteamine is derived from coenzyme A degradation, although its plasma concentrations are low. Two formulations of cysteamine have been approved for the treatment of cystinosis, in which cysteamine is prescribed to decrease intra lysosomal cystine accumulation. The odors of thiols, particularly those of low molecular weight such as cysteamine, are often strong and repulsive. (Besouw et al., *Drug Discovery Today* 18, (2013) 785).

Thiol drugs such as NAC and cysteamine exert their activity inside of the cell. What is needed are novel strategies which permit intracellular delivery of LMW thiols. Such an approach will reduce the total dose and reduce the frequency of dosing. Administration of LMW thiols intracellularly may lead treatment of cystinuria, cystinosis, cancer, neurodegenerative disease, Parkinson's disease, Huntington's disease, malaria, nonalcoholic fatty liver disease, radiation poisoning, arsenic poisoning, Wilson's disease or rheumatoid arthritis (doi.org/10.1016/j.nbd.2019.104530) and optimize many clinical applications of these compounds. (Annalise R. et al., *Mini-Reviews in Medicinal Chemistry*, (2019)1).

SUMMARY

The present disclosure satisfies these and other needs by providing in one aspect a compound of Formula (I):

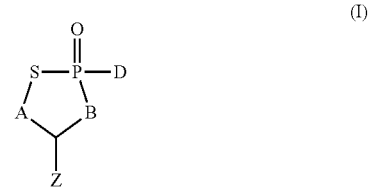

(I)

or pharmaceutically acceptable salts, hydrates or solvate thereof where D is —NR$_7$R$_8$; A is —CHR$_9$, —CHR$_{10}$CHR$_{11}$, —CHR$_{12}$CHR$_{13}$CHR$_{14}$; B is —S—, NR$_{15}$ or —CH$_2$NR$_{31}$; Z is —H, alkyl, substituted alkyl, alkenyl, substituted alkenyl, —CO$_2$R$_{16}$, —CO$_2$NR$_{17}$R$_{18}$, —CH$_2$OR$_{19}$ or —CN; R$_7$ and R$_8$ are independently —H, alkyl, substituted alkyl, alkenyl, substituted alkenyl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, aryl, substituted aryl, arylalkyl, substituted arylalkyl, arylalkenyl, substituted arylalkenyl, heteroalkyl, substituted heteroalkyl, heteroalkenyl, substituted heteroalkenyl, heteroaryl, substituted heteroaryl, heteroarylalkyl, substituted heteroarylalkyl, heteroarylalkenyl, substituted heteroarylalkenyl or R$_7$ and R$_8$ together with the atoms to which they are attached form a cycloalkyl, substituted cycloalkyl, cycloalkenyl, substituted cycloalkenyl heterocycloalkyl, substituted heterocycloalkyl, heterocycloalkenyl or substituted heterocycloalkenyl ring; R$_{15}$ is —H, alkyl, substituted alkyl, alkenyl, substituted alkenyl, aryl, substituted aryl, arylalkyl, substituted arylalkyl, heteroaryl, substituted heteroaryl, heteroarylalkyl, substituted heteroarylalkyl; R$_{16}$, R$_{19}$, R$_{20}$, R$_{23}$, R$_{24}$, R$_{27}$, R$_{28}$ and R$_{31}$ are independently —H, alkyl, substituted alkyl, alkenyl, substituted alkenyl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, aryl, substituted aryl, arylalkyl, substituted arylalkyl, arylalkenyl, substituted arylalkenyl, heteroalkyl, substituted heteroalkyl, heteroalkenyl, substituted heteroalkenyl, heteroaryl, substituted heteroaryl, heteroarylalkyl, substituted heteroarylalkyl, heteroarylalkenyl or substituted heteroarylalkyl; $R_9$ is —H, alkyl, alkenyl, aryl, —$CO_2R_{20}$, —$CO_2NR_{21}R_{22}$, —$CH_2OR_{23}$ or —CN; $R_{10}$ and $R_{11}$ are independently —H, alkyl, alkenyl, —$CO_2R_{24}$, —$CO_2NR_{25}R_{26}$, —$CH_2OR_{27}$, —CN or $R_{10}$ and $R_{11}$ together with the atoms to which they are attached form a cycloalkyl, substituted cycloalkyl, cycloalkenyl, substituted cycloalkenyl, cycloheteroalkyl, substituted cycloheteroalkyl, cycloheteroalkenyl or substituted cycloheteroalkenyl ring; $R_{12}$, $R_{13}$ and $R_{14}$ are independently —H, alkyl, alkenyl, —$CO_2R_{28}$, —$CO_2NR_{29}R_{30}$, —$CH_2OR_{31}$, —CN or $R_{12}$ and $R_{13}$ together with the atoms to which they are attached form a cycloalkyl, substituted cycloalkyl, cycloalkenyl, substituted cycloalkenyl, cycloheteroalkyl, substituted cycloheteroalkyl, cycloheteroalkenyl or substituted cycloheteroalkenyl ring, or $R_{13}$ and $R_{14}$ together with the atoms to which they are attached form a cycloalkyl, substituted cycloalkyl, cycloalkenyl, substituted cycloalkenyl, cycloheteroalkyl, substituted cycloheteroalkyl, cycloheteroalkenyl or substituted cycloheteroalkenyl ring or $R_{10}$ and Ria together with the atoms to which they are attached form a cycloalkyl, substituted cycloalkyl, cycloalkenyl, substituted cycloalkenyl, cycloheteroalkyl, substituted cycloheteroalkyl, cycloheteroalkenyl or substituted cycloheteroalkenyl ring; $R_{17}$ and $R_{18}$ are independently —H, alkyl, substituted alkyl, alkenyl, substituted alkenyl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, aryl, substituted aryl, arylalkyl, substituted arylalkyl, arylalkenyl, substituted arylalkenyl, heteroalkyl, heteroalkenyl, heteroaryl, substituted heteroaryl, heteroarylalkyl, substituted heteroarylalkyl, heteroarylalkenyl or substituted heteroarylalkyl or $R_{17}$ and $R_{18}$ together with the atoms to which they are attached form a cycloalkyl, substituted cycloalkyl, cycloalkenyl, substituted cycloalkenyl, cycloheteroalkyl, substituted cycloheteroalkyl, cycloheteroalkenyl or substituted cycloheteroalkenyl ring; $R_{21}$ and $R_{22}$ are independently —H, alkyl, substituted alkyl, alkenyl, substituted alkenyl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, aryl, substituted aryl, arylalkyl, substituted arylalkyl, arylalkenyl, substituted arylalkenyl, heteroalkyl, heteroalkenyl, heteroaryl, substituted heteroaryl, heteroarylalkyl, substituted heteroarylalkyl, heteroarylalkenyl, substituted heteroarylalkyl or $R_{21}$ and $R_{22}$ together with the atoms to which they are attached form a cycloalkyl, substituted cycloalkyl, cycloalkenyl, substituted cycloalkenyl, cycloheteroalkyl, substituted cycloheteroalkyl, cycloheteroalkenyl or substituted cycloheteroalkenyl ring; $R_{25}$ and $R_{26}$ are independently —H, alkyl, substituted alkyl, alkenyl, substituted alkenyl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, aryl, substituted aryl, arylalkyl, substituted arylalkyl, arylalkenyl, substituted arylalkenyl, heteroalkyl, heteroalkenyl, heteroaryl, substituted heteroaryl, heteroarylalkyl, substituted heteroarylalkyl, heteroarylalkenyl, substituted heteroarylalkyl or $R_{25}$ and $R_{26}$ together with the atoms to which they are attached form a cycloalkyl, substituted cycloalkyl, cycloalkenyl, substituted cycloalkenyl, cycloheteroalkyl, substituted cycloheteroalkyl, cycloheteroalkenyl or substituted cycloheteroalkenyl ring; $R_{29}$ and $R_{30}$ are independently —H, alkyl, substituted alkyl, alkenyl, substituted alkenyl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, aryl, substituted aryl, arylalkyl, substituted arylalkyl, arylalkenyl, substituted arylalkenyl, heteroalkyl, heteroalkenyl, heteroaryl, substituted heteroaryl, heteroarylalkyl, substituted heteroarylalkyl, heteroarylalkenyl, substituted heteroarylalkyl or $R_{27}$ and $R_{28}$ together with the atoms to which they are attached form a cycloalkyl, substituted cycloalkyl, cycloalkenyl, substituted cycloalkenyl, cycloheteroalkyl, substituted cycloheteroalkyl, cycloheteroalkenyl or substituted cycloheteroalkenyl ring; and $R_{31}$ is —H or alkyl; provided that $R_7$ and $R_8$ are not both —H.

Also provided are derivatives, including salts, esters, enol ethers, enol esters, solvates, hydrates, metabolites and prodrugs of the compounds described herein. Further provided are pharmaceutical compositions which include the compounds provided herein and a pharmaceutically acceptable vehicle.

Methods of treating, preventing, or ameliorating symptoms of medical disorders such as, for example, cystinuria, cystinosis, cancer neurodegenerative disease, Parkinson's disease, Huntington's disease, malaria, nonalcoholic fatty liver disease, radiation poisoning, arsenic poisoning, Wilson's disease or rheumatoid arthritis are also provided herein.

DETAILED DESCRIPTION

Definitions

Unless defined otherwise, all technical and scientific terms used herein have the same meaning as is commonly understood by one of ordinary skill in the art to which this invention belongs. If a plurality of definitions for a term exist herein, those in this section prevail unless stated otherwise.

As used herein, and unless otherwise specified, the terms "about" and "approximately," when used in connection with a property with a numeric value or range of values indicate that the value or range of values may deviate to an extent deemed reasonable to one of ordinary skill in the art while still describing the particular property. Specifically, the terms "about" and "approximately," when used in this context, indicate that the numeric value or range of values may vary by 5%, 4%, 3%, 2%, 1%, 0.9%, 0.8%, 0.7%, 0.6%, 0.5%, 0.4%, 0.3%, 0.2% or 0.1% of the recited value or range of values.

"Alkyl," by itself or as part of another substituent, refers to a saturated or unsaturated, branched, straight-chain or cyclic monovalent hydrocarbon radical derived by the removal of one hydrogen atom from a single carbon atom of a parent alkane. Typical alkyl groups include, but are not limited to, methyl; ethyls; propyls such as propan-1-yl, propan-2-yl, etc.; butyls such as butan-1-yl, butan-2-yl, 2-methyl-propan-1-yl, 2-methyl-propan-2-yl, etc.; and the like. In some embodiments, an alkyl group comprises from 1 to 20 carbon atoms ($C_1$-$C_{20}$ alkyl). In other embodiments, an alkyl group comprises from 1 to 10 carbon atoms ($C_1$-$C_{10}$ alkyl). In still other embodiments, an alkyl group comprises from 1 to 6 carbon atoms ($C_1$-$C_6$ alkyl).

"Alkenyl," by itself or as part of another substituent, refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-di en-1-yl, buta-1,3-di en-2-yl, cyclobut-1-en-1-yl, cyclobut-1-en-3-yl, cyclobuta-1,3-dien-1-yl, etc.; and the like.

"Alkynyl," by itself or as part of another substituent refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Aryl," by itself or as part of another substituent, refers to a monovalent aromatic hydrocarbon group derived by the removal of one hydrogen atom from a single carbon atom of a parent aromatic ring system, as defined herein. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In some embodiments, an aryl group comprises from 6 to 20 carbon atoms ($C_6$-$C_{20}$ aryl). In other embodiments, an aryl group comprises from 6 to 15 carbon atoms ($C_6$-$C_{15}$ aryl). In still other embodiments, an aryl group comprises from 6 to 10 carbon atoms ($C_6$-$C_{10}$ aryl).

"Arylalkyl," by itself or as part of another substituent, refers to an acyclic alkyl group in which one of the hydrogen atoms bonded to a carbon atom, typically a terminal or spa carbon atom, is replaced with an aryl group as, as defined herein. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. In some embodiments, an arylalkyl group is ($C_6$-$C_{30}$) arylalkyl, e.g., the alkyl moiety of the arylalkyl group is ($C_1$-$C_{10}$) alkyl and the aryl moiety is ($C_6$-$C_{20}$) aryl. In other embodiments, an arylalkyl group is ($C_6$-$C_{20}$) arylalkyl, e.g., the alkyl moiety of the arylalkyl group is ($C_1$-$C_8$) alkyl and the aryl moiety is ($C_6$-$C_{12}$) aryl. In still other embodiments, an arylalkyl group is ($C_6$-$C_{15}$) arylalkyl, e.g., the alkyl moiety of the arylalkyl group is ($C_1$-05) alkyl and the aryl moiety is ($C_6$-$C_{10}$) aryl.

"Arylalkenyl," by itself or as part of another substituent, refers to an acyclic alkenyl group in which one of the hydrogen atoms bonded to a carbon atom, is replaced with an aryl group as, as defined herein.

"Cycloalkyl," by itself or as part of another substituent, refers to a saturated cyclic monovalent hydrocarbon radical derived by the removal of one hydrogen atom from a single carbon atom of a parent cycloalkane. Typical cycloalkyl groups include, but are not limited to, cyclopropyl, cyclobutyl, cyclopentyl cycopentenyl; etc.; and the like. In some embodiments, a cycloalkyl group comprises from 3 to 20 carbon atoms ($C_1$-$C_{15}$ alkyl). In other embodiments, a cycloalkyl group comprises from 3 to 10 carbon atoms ($C_1$-$C_{10}$ alkyl). In still other embodiments, a cycloaklyl group comprises from 3 to 8 carbon atoms ($C_1$-$C_8$ alkyl). The term 'cyclic monovalent hydrocarbon radical" also includes multicyclic hydrocarbon ring systems having a single radical and between 3 and 12 carbon atoms. Exemplary multicyclic cycloalkyl rings include, for example, norbornyl, pinyl, and adamantyl.

"Cycloalkenyl," by itself or as part of another substituent, refers to an unsaturated cyclic monovalent hydrocarbon radical derived by the removal of one hydrogen atom from a single carbon atom of a parent cycloalkene. Typical cycloalkyl groups include, but are not limited to, cyclopropene, cyclobutene cyclopentene; etc.; and the like. In some embodiments, a cycloalkenyl group comprises from 3 to 20 carbon atoms ($C_1$-$C_{20}$ alkenyl). In other embodiments, a cycloalkenyl group comprises from 3 to 10 carbon atoms ($C_1$-$C_{10}$ alkenyl). In still other embodiments, a cycloalkenyl group comprises from 3 to 8 carbon atoms ($C_1$-$C_8$ alkenyl). The term 'cyclic monovalent hydrocarbon radical" also includes multicyclic hydrocarbon ring systems having a single radical and between 3 and 12 carbon atoms with an alkenyl group "Cycloheteroalkyl," by itself or as part of another substituent, refers to a cycloalkyl group as defined herein in which one or more one or more of the carbon atoms (and optionally any associated hydrogen atoms), are each, independently of one another, replaced with the same or different heteroatoms or heteroatomic groups as defined in "heteroalkyl" below.

"Cycloheteroalkenyl," by itself or as part of another substituent, refers to a cycloalkenyl group as defined herein in which one or more one or more of the carbon atoms (and optionally any associated hydrogen atoms), are each, independently of one another, replaced with the same or different heteroatoms or heteroatomic groups as defined in "heteroalkenyl" below.

"Compounds," refers to compounds encompassed by structural formulae disclosed herein and includes any specific compounds within these formulae whose structure is disclosed herein. Compounds may be identified either by their chemical structure and/or chemical name. The chemical structure is determinative of the identity of the compound. The compounds described herein may contain one or more chiral centers and/or double bonds and therefore, may exist as stereoisomers, such as double-bond isomers (i.e., geometric isomers), enantiomers or diastereomers. Accordingly, the chemical structures depicted herein encompass the stereoisomerically pure form depicted in the structure (e.g., geometrically pure, enantiomerically pure or diastereomerically pure). The chemical structures depicted herein also encompass the enantiomeric and stereoisomeric derivatives of the compound depicted. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that may be incorporated into the compounds disclosed herein include, but are not limited to, $^2$H, $^3$H, $^{11}$C, $^{13}$C, $^{14}$C, $^{15}$N, $^{18}$O, $^{17}$O, etc.

Compounds may exist in unsolvated forms as well as solvated forms, including hydrated forms. In general, compounds may be hydrated or solvated. Certain compounds may exist in multiple crystalline or amorphous forms. In general, all physical forms are equivalent for the uses contemplated herein and are intended to be within the scope of the present disclosure. Further, it should be understood, when partial structures of the compounds are illustrated, that brackets indicate the point of attachment of the partial structure to the rest of the molecule.

"Halo," by itself or as part of another substituent refers to a radical —F, —Cl, —Br or —I.

"Heteroalkyl," refer to an alkyl, group, in which one or more of the carbon atoms (and optionally any associated hydrogen atoms), are each, independently of one another, replaced with the same or different heteroatoms or heteroatomic groups. Typical heteroatoms or heteroatomic groups which can replace the carbon atoms include, but are not limited to, —O—, —S—, —N—, —Si—, —NH—, —S(O)—, —S(O)$_2$—, —S(O)NH—, —S(O)$_2$NH— and the like and combinations thereof. The heteroatoms or heteroatomic groups may be placed at any interior position of the alkyl, alkenyl or alkynyl groups. Typical heteroatomic groups which can be included in these groups include, but are not limited to, —O—, —S—, —O—O—, —S—S—, —O—S—, —NR$^{501}$R$^{502}$, =N—N=, —N=N—, —N=N—NR$^{503}$R$^{404}$, —PR$^{505}$—, —P(O)$_2$—, —POR$^{506}$—, —O—P(O)$_2$—, —SO—, —SO$_2$—, —SnR$^{507}$R$^{508}$ and the like, where R$^{501}$, R$^{502}$, R$^{503}$, R$^{504}$, R$^{505}$, R$^{506}$, R$^{507}$ and R$^{508}$ are independently hydrogen, alkyl, aryl, substituted aryl, heteroalkyl, heteroaryl or substituted heteroaryl.

"Heteroalkenyl," refers to an alkenyl group in which one or more of the carbon atoms (and optionally any associated hydrogen atoms), are each, independently of one another, replaced with the same or different heteroatoms or heteroatomic groups. Typical heteroatoms or heteroatomic groups which can replace the carbon atoms include, but are not limited to, —O—, —S—, —N—, —Si—, —NH—, —S(O)—, —S(O)$_2$—, —S(O)NH—, —S(O)$_2$NH— and the like and combinations thereof. The heteroatoms or heteroatomic groups may be placed at any interior position of the alkyl, alkenyl or alkynyl groups. Typical heteroatomic groups which can be included in these groups include, but are not limited to, —O—, —S—, —O—O—, —S—S—, —O—S—, —NR$^{501}$R$^{502}$, =N—N=, —N=N—, —N=N—NR$^{503}$R$^{404}$, —PR$^{505}$—, —P(O)$_2$—, —POR$^{506}$—, —O—P(O)$_2$—, —SO—, —SO$_2$—, —SnR$^{507}$R$^{508}$ and the like, where R$^{501}$, R$^{502}$, R$^{503}$, R$^{504}$, R$^{505}$, R$^{506}$, R$^{507}$ and R$^{508}$ are independently hydrogen, alkyl, aryl, substituted aryl, heteroalkyl, heteroaryl or substituted heteroaryl.

"Heteroaryl," by itself or as part of another substituent, refers to a monovalent heteroaromatic radical derived by the removal of one hydrogen atom from a single atom of a parent heteroaromatic ring systems, as defined herein. Typical heteroaryl groups include, but are not limited to, groups derived from acridine, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryl group comprises from 5 to 20 ring atoms (5-20 membered heteroaryl). In other embodiments, the heteroaryl group comprises from 5 to 10 ring atoms (5-10 membered heteroaryl). Exemplary heteroaryl groups include those derived from furan, thiophene, pyrrole, benzothiophene, benzofuran, benzimidazole, indole, pyridine, pyrazole, quinoline, imidazole, oxazole, isoxazole and pyrazine.

"Heteroarylalkyl," by itself or as part of another substituent refers to an acyclic alkyl group in which one of the hydrogen atoms bonded to a carbon atom, typically a terminal or spa carbon atom, is replaced with a heteroaryl group. In some embodiments, the heteroarylalkyl group is a 6-21 membered heteroarylalkyl, e.g., the alkyl moiety of the heteroarylalkyl is (C$_1$-C$_6$) alkyl and the heteroaryl moiety is a 5-15-membered heteroaryl. In other embodiments, the heteroarylalkyl is a 6-13 membered heteroarylalkyl, e.g., the alkyl moiety is (C$_1$-C$_3$) alkyl and the heteroaryl moiety is a 5-10 membered heteroaryl.

"Heteroarylalkenyl," by itself or as part of another substituent refers to an acyclic alkenyl group in which one of the hydrogen atoms bonded to a carbon atom, is replaced with a heteroaryl group.

"Hydrates," refers to incorporation of water into to the crystal lattice of a compound described herein, in stoichiometric proportions, resulting in the formation of an addict. Methods of making hydrates include, but are not limited to, storage in an atmosphere containing water vapor, dosage forms that include water, or routine pharmaceutical processing steps such as, for example, crystallization (i.e., from water or mixed aqueous solvents), lyophilization, wet granulation, aqueous film coating, or spray drying. Hydrates may also be formed, under certain circumstances, from crystalline solvates upon exposure to water vapor, or upon suspension of the anhydrous material in water. Hydrates may also crystallize in more than one form resulting in hydrate polymorphism. See e.g., (Guillory, K., Chapter 5, pp. 202205 in *Polymorphism in Pharmaceutical Solids*, (Brittain, H. ed.), Marcel Dekker, Inc., New York, NY, 1999). The above methods for preparing hydrates are well within the ambit of those of skill in the art, are completely conventional and do not require any experimentation beyond what is typical in the art. Hydrates may be characterized and/or analyzed by methods well known to those of skill in the art such as, for example, single crystal X-ray diffraction, X-ray powder diffraction, polarizing optical microscopy, thermal microscopy, thermogravimetry, differential thermal analysis, differential scanning calorimetry, IR spectroscopy, Raman spectroscopy and NMR spectroscopy. (Brittain, H., Chapter 6, pp. 205208 in *Polymorphism in Pharmaceutical Solids*, (Brittain, H. ed.), Marcel Dekker, Inc. New York, 1999). In addition, many commercial companies routine offer services that include preparation and/or characterization of hydrates such as, for example, HOLODIAG, Pharmaparc II, Voie de l'Innovation, 27 100 Val de Reuil, France (www.holodiag.com).

"Parent Aromatic Ring System," refers to an unsaturated cyclic or polycyclic ring system having a conjugated p electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Parent Heteroaromatic Ring System," refers to a parent aromatic ring system in which one or more carbon atoms (and optionally any associated hydrogen atoms) are each independently replaced with the same or different heteroatom. Typical heteroatoms to replace the carbon atoms include, but are not limited to, N, P, O, S, Si, etc. Specifically included within the definition of "parent heteroaromatic ring system" are fused ring systems in which one or more of the rings are aromatic and one or more of the rings are saturated or unsaturated, such as, for example, benzodioxan, benzofuran, chromane, chromene, indole, indoline, xanthene, etc. Typical parent heteroaromatic ring systems include, but are not limited to, arsindole, carbazole, b-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

"Pharmaceutically acceptable salt," refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Prodrug" as used herein, refers to a derivative of a drug molecule that requires a transformation within the body to release the active drug. Prodrugs are frequently, although not necessarily, pharmacologically inactive until converted to the parent drug.

"Promoiety" as used herein, refers to a form of protecting group that when used to mask a functional group within a drug molecule converts the drug into a prodrug. Typically, the promoiety will be attached to the drug via bond(s) that are cleaved by enzymatic or non-enzymatic means in vivo.

"Protecting group," refers to a grouping of atoms that when attached to a reactive functional group in a molecule masks, reduces or prevents reactivity of the functional group during chemical synthesis. Examples of protecting groups can be found in Green et al., "Protective Groups in Organic Chemistry", (Wiley, 2nd ed. 1991) and Harrison et al., "Compendium of Synthetic Organic Methods", Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Solvates," refers to incorporation of solvents into to the crystal lattice of a compound described herein, in stoichiometric proportions, resulting in the formation of an adduct. Methods of making solvates include, but are not limited to, storage in an atmosphere containing a solvent, dosage forms that include the solvent, or routine pharmaceutical processing steps such as, for example, crystallization (i.e., from solvent or mixed solvents) vapor diffusion, etc. Solvates may also be formed, under certain circumstances, from other crystalline solvates or hydrates upon exposure to the solvent or upon suspension material in solvent. Solvates may crystallize in more than one form resulting in solvate polymorphism. See e.g., (Guillory, K., Chapter 5, pp. 205208 in *Polymorphism in Pharmaceutical Solids*, (Brittain, H. ed.), Marcel Dekker, Inc., New York, NY, 1999)). The above methods for preparing solvates are well within the ambit of those of skill in the art, are completely conventional do not require any experimentation beyond what is typical in the art. Solvates may be characterized and/or analyzed by methods well known to those of skill in the art such as, for example, single crystal X-ray diffraction, X-ray powder diffraction, polarizing optical microscopy, thermal microscopy, thermogravimetry, differential thermal analysis, differential scanning calorimetry, IR spectroscopy, Raman spectroscopy and NMR spectroscopy. (Brittain, H., Chapter 6, pp. 205208 in *Polymorphism in Pharmaceutical Solids*, (Brittain, H. ed.), Marcel Dekker, Inc. New York, 1999). In addition, many commercial companies routine offer services that include preparation and/or characterization of solvates such as, for example, HOLODIAG, Pharmaparc II, Voie de l'Innovation, 27 100 Val de Reuil, France (www.holodiag-.com).

"Substituted," when used to modify a specified group or radical, means that one or more hydrogen atoms of the specified group or radical are each, independently of one another, replaced with the same or different substituent(s). Substituent groups useful for substituting saturated carbon atoms in the specified group or radical include $R^a$, halo, —O—, =O, —OR$^b$, —SR$^b$, —S—, =S, —NR$^c$R$^c$, =NR$^b$, =N—OR$^b$, trihalomethyl, —CF$_3$, —CN, —OCN, —SCN, —NO, —NO$_2$, —N—OR$^b$, —N—NR$^c$R$^c$, —NR$^b$S(O)$_2$R$^b$, =N$_2$, —N$_3$, —S(O)$_2$R$^b$, —S(O)$_2$R$^b$R$^b$, —S(O)$_2$O—, —S(O)$_2$OR$^b$, —OS(O)$_2$R$^b$—, —OS(O)$_2$O—, —OS(O)$_2$OR$_2$, —OS(O)$_2$NR$^c$NR$^c$, —P(O)(O$^-$)$_2$, —P(O)(OR$^b$)(O$^-$), —P(O)(OR$^b$)(OR$^b$), —C(O)R$^b$, —C(O)NR$^b$—OR$^b$—C(S) R$^b$, —C(NR$^b$)R$^b$, —C(O)O—, —C(O)OR$^b$, —C(S)OR$^b$, —C(O)NR$^c$R$^c$, —C(NR$^b$)NR$^c$R$^c$, —OC(O)R$^b$, —OC(S) R$^b$, —OC(O)O—, —OC(O)OR$^b$, —OC(O)NR$^c$R$^c$, —OC(NCN)NR$^c$R$^c$—OC(S)OR$^b$, —NR$^b$C(O)R$^b$, —NR$^b$C(S)R$^b$, —NR$^b$C(O)O—, —NR$^b$C(O)OR$^b$, —NR$^b$C(NCN)OR$^b$, —NR$^b$S(O)$_2$NR$^c$R$^c$, —NR$^b$C(S)OR$^b$, —NR$^b$C(O)NR$^c$R$^c$, —NR$^b$C(S)NR$^c$R$^c$, —NR$^b$C(S)NR$^c$C(O)R$^a$, —NR$^b$S(O)$_2$OR$^b$, —NR$^b$S(O)$_2$R$^b$, —NR$^b$C(NCN) NR$^c$R$^c$, —NR$^b$C(NR$^b$)R$^b$ and —NR$^b$C(NR$^b$)NR$^c$R$^c$, where each $R^a$ is independently, aryl, substituted aryl, heteroalkyl, substituted heteroalkyl, heteroaryl or substituted heteroaryl; each $R^b$ is independently hydrogen, alkyl, heteroalkyl, substituted heteroalkyl, arylalkyl, substituted arylalkyl, heteroarylalkyl or substituted heteroarylalkyl; and each $R^c$ is independently $R^b$ or alternatively, the two $R^c$s taken together with the nitrogen atom to which they are bonded form a 4-, 5-, 6- or 7 membered-cycloheteroalkyl, substituted cycloheteroalkyl or a cycloheteroalkyl fused with an aryl group which may optionally include from 1 to 4 of the same or different additional heteroatoms selected from the group consisting of O, N and S. As specific examples, —$NR^cR^c$ is meant to include —$NH_2$, —NH-alkyl, N-pyrrolidinyl and N-morpholinyl. In other embodiments, substituent groups useful for substituting saturated carbon atoms in the specified group or radical include $R^a$, halo, —$OR^b$, —$NR^cR^c$, trihalomethyl, —CN, —$NR^bS(O)_2R^b$, —$C(O)R^b$, —$C(O)NR^b$—$OR^b$, —$C(O)OR^b$, —$C(O)NR^cR^c$, —$OC(O)R^b$, —$OC(O)OR^b$, —$OS(O)_2NR^cNR^c$, —$OC(O)NR^cNR^c$, and —$NR^bC(O)OR^b$, where each $R^a$ is independently alkyl, aryl, heteroaryl, each $R^b$ is independently hydrogen, $R^a$, heteroalkyl, arylalkyl, heteroarylalkyl; and each $R^c$ is independently $R^b$ or alternatively, the two $R^c$s taken together with the nitrogen atom to which they are bonded form a 4-, 5-, 6 or -7 membered-cycloheteroalkyl ring.

Substituent groups useful for substituting unsaturated carbon atoms in the specified group or radical include —$R^a$, halo, —O—, —$OR^b$, —$SR^b$, —S—, —$NR^cR^c$, trihalomethyl, —$CF_3$, —CN, —OCN, —SCN, —NO, —$NO_2$, —$N_3$, —$S(O)_2O$—, —$S(O)_2OR^b$, —$OS(O)_2R^b$, —$OS(O)_2OR^b$, —$OS(O)_2O^-$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$OC(O)NR^cR^c$, —$OS(O)_2NR^cNR^c$, —$NR^bC(O)R^b$, —$NR^bC(S)R^b$, —$NR^bC(O)O^-$, —$NR^bC(O)OR^b$, —$NR^bS(O)_2OR^a$, —$NR^bS(O)_2R^a$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined. In other embodiments, substituent groups useful for substituting unsaturated carbon atoms in the specified group or radical include —$R^a$, halo, —$OR^b$, —$SR^b$, —$NR^cR^c$, trihalomethyl, —CN, —$S(O)_2OR^b$, —$C(O)R^b$, —$C(O)OR^b$, —$C(O)NR^cR^c$, —$OC(O)R^b$, —$OC(O)OR^b$, —$OS(O)_2NNR^cNR^c$, —$NR^bC(O)R^b$ and —$NR^bC(O)OR^b$, where $R^a$, $R^b$ and $R^c$ are as previously defined.

Substituent groups useful for substituting nitrogen atoms in heteroalkyl and cycloheteroalkyl groups include, but are not limited to, —$R^a$, —O—, —$OR^b$, —$SR^b$, —S—, —$NR^cR^c$, trihalomethyl, —$CF_3$, —CN, —NO, —$NO_2$, —$S(O)_2R^b$, —$S(O)_2O$—, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)OR^b$, —$OC(S)OR^b$, —$NR^bC(O)R^b$, —$NR^bC(S)R^b$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined. In some embodiments, substituent groups useful for substituting nitrogen atoms in heteroalkyl and cycloheteroalkyl groups include, $R^a$, halo, —$OR^b$, —$NR^cR^c$, trihalomethyl, —CN, —$S(O)_2OR^b$, —$OS(O)_2R^b$, —$OS(O)_2OR^b$, —$C(O)R^b$, —$C(NR^b)R^b$, —$C(O)OR^b$, —$C(O)NR^cR^c$, —$OC(O)R^b$, —$OC(O)OR^b$, —$OS(O)_2NR^cNR^c$, —$NR^bC(O)R^b$ and —$NR^bC(O)OR^b$, where $R^a$, $R^b$ and $R^c$ are as previously defined.

Substituent groups from the above lists useful for substituting other specified groups or atoms will be apparent to those of skill in the art.

The substituents used to substitute a specified group can be further substituted, typically with one or more of the same or different groups selected from the various groups specified above.

"Vehicle," refers to a diluent, excipient or carrier with which a compound is administered to a subject. In some embodiments, the vehicle is diagnostically acceptable Reference will now be made in detail to particular embodiments of compounds and methods. The disclosed embodiments are not intended to be limiting of the claims. To the contrary, is the claims are intended to cover all alternatives, modifications and equivalents.

Compounds

Provided herein are compound of structural Formula (I):

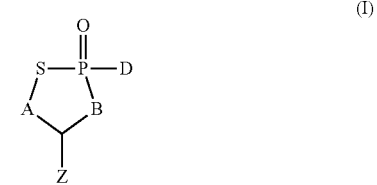

or pharmaceutically acceptable salts, hydrates or solvate thereof wherein:

D is —$NR_7R_8$; A is —$CHR_9$, —$CHR_{10}CHR_{11}$, —$CHR_{12}CHR_{13}CHR_{14}$; B is —S—, $NR_{15}$ or —$CH_2NR_{31}$, Z is —H, alkyl, substituted alkyl, alkenyl, substituted alkenyl, —$CO_2R_{16}$, —$CO_2NR_{17}R_{18}$, —$CH_2OR_{19}$ or —CN; $R_7$ and $R_8$ are independently —H, alkyl, substituted alkyl, alkenyl, substituted alkenyl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, aryl, substituted aryl, arylalkyl, substituted arylalkyl, arylalkenyl, substituted arylalkenyl, heteroalkyl, substituted heteroalkyl, heteroalkenyl, substituted heteroalkenyl, heteroaryl, substituted heteroaryl, heteroarylalkyl, substituted heteroarylalkyl, heteroarylalkenyl, substituted heteroarylalkenyl or $R_7$ and $R_8$ together with the atoms to which they are attached form a cycloalkyl, substituted cycloalkyl, cycloalkenyl, substituted cycloalkenyl heterocycloalkyl, substituted heterocycloalkyl, heterocycloalkenyl or substituted heterocycloalkenyl ring; $R_{15}$ is —H, alkyl, substituted alkyl, alkenyl, substituted alkenyl, aryl, substituted aryl, arylalkyl, substituted arylalkyl, heteroaryl, substituted heteroaryl, heteroarylalkyl, substituted heteroarylalkyl; $R_{16}$, $R_{19}$, $R_{20}$, $R_{23}$, $R_{24}$, $R_{27}$, $R_{28}$ and $R_{31}$ are independently —H, alkyl, substituted alkyl, alkenyl, substituted alkenyl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, aryl, substituted aryl, arylalkyl, substituted arylalkyl, arylalkenyl, substituted arylalkenyl, heteroalkyl, substituted heteroalkyl, heteroalkenyl, substituted heteroalkenyl, heteroaryl, substituted heteroaryl, heteroarylalkyl, substituted heteroarylalkyl, heteroarylalkenyl or substituted heteroarylalkyl; $R_9$ is —H, alkyl, alkenyl, aryl, —$CO_2R_{20}$, —$CO_2NR_{21}R_{22}$, —$CH_2OR_{23}$ or —CN; $R_{10}$ and $R_{11}$ are independently —H, alkyl, alkenyl, —$CO_2R_{24}$, —$CO_2NR_{25}R_{26}$, —$CH_2OR_{27}$, —CN or $R_{10}$ and $R_{11}$ together with the atoms to which they are attached form a cycloalkyl, substituted cycloalkyl, cycloalkenyl, substituted cycloalkenyl, cycloheteroalkyl, substituted cycloheteroalkyl, cycloheteroalkenyl or substituted cycloheteroalkenyl ring; $R_{12}$, $R_{13}$ and $R_{14}$ are independently —H, alkyl, alkenyl, —CO$_2$R$_{28}$, —CO$_2$NR$_{29}$R$_{30}$, —CH$_2$OR$_{31}$, —CN or $R_{12}$ and $R_{13}$ together with the atoms to which they are attached form a cycloalkyl, substituted cycloalkyl, cycloalkenyl, substituted cycloalkenyl, cycloheteroalkyl, substituted cycloheteroalkyl, cycloheteroalkenyl or substituted cycloheteroalkenyl ring, or $R_{13}$ and $R_{14}$ together with the atoms to which they are attached form a cycloalkyl, substituted cycloalkyl, cycloalkenyl, substituted cycloalkenyl, cycloheteroalkyl, substituted cycloheteroalkyl, cycloheteroalkenyl or substituted cycloheteroalkenyl ring or $R_{10}$ and $R_{12}$ together with the atoms to which they are attached form a cycloalkyl, substituted cycloalkyl, cycloalkenyl, substituted cycloalkenyl, cycloheteroalkyl, substituted cycloheteroalkyl, cycloheteroalkenyl or substituted cycloheteroalkenyl ring; $R_{17}$ and $R_{18}$ are independently —H, alkyl, substituted alkyl, alkenyl, substituted alkenyl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, aryl, substituted aryl, arylalkyl, substituted arylalkyl, arylalkenyl, substituted arylalkenyl, heteroalkyl, heteroalkenyl, heteroaryl, substituted heteroaryl, heteroarylalkyl, substituted heteroarylalkyl, heteroarylalkenyl or substituted heteroarylalkyl or $R_{17}$ and $R_{18}$ together with the atoms to which they are attached form a cycloalkyl, substituted cycloalkyl, cycloalkenyl, substituted cycloalkenyl, cycloheteroalkyl, substituted cycloheteroalkyl, cycloheteroalkenyl or substituted cycloheteroalkenyl ring; $R_{21}$ and $R_{22}$ are independently —H, alkyl, substituted alkyl, alkenyl, substituted alkenyl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, aryl, substituted aryl, arylalkyl, substituted arylalkyl, arylalkenyl, substituted arylalkenyl, heteroalkyl, heteroalkenyl, heteroaryl, substituted heteroaryl, heteroarylalkyl, substituted heteroarylalkyl, heteroarylalkenyl, substituted heteroarylalkyl or $R_{21}$ and $R_{22}$ together with the atoms to which they are attached form a cycloalkyl, substituted cycloalkyl, cycloalkenyl, substituted cycloalkenyl, cycloheteroalkyl, substituted cycloheteroalkyl, cycloheteroalkenyl or substituted cycloheteroalkenyl ring; $R_{25}$ and $R_{26}$ are independently —H, alkyl, substituted alkyl, alkenyl, substituted alkenyl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, aryl, substituted aryl, arylalkyl, substituted arylalkyl, arylalkenyl, substituted arylalkenyl, heteroalkyl, heteroalkenyl, heteroaryl, substituted heteroaryl, heteroarylalkyl, substituted heteroarylalkyl, heteroarylalkenyl, substituted heteroarylalkyl or $R_{25}$ and $R_{26}$ together with the atoms to which they are attached form a cycloalkyl, substituted cycloalkyl, cycloalkenyl, substituted cycloalkenyl, cycloheteroalkyl, substituted cycloheteroalkyl, cycloheteroalkenyl or substituted cycloheteroalkenyl ring; $R_{29}$ and $R_{30}$ are independently —H, alkyl, substituted alkyl, alkenyl, substituted alkenyl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, aryl, substituted aryl, arylalkyl, substituted arylalkyl, arylalkenyl, substituted arylalkenyl, heteroalkyl, heteroalkenyl, heteroaryl, substituted heteroaryl, heteroarylalkyl, substituted heteroarylalkyl, heteroarylalkenyl, substituted heteroarylalkyl or $R_{27}$ and $R_{28}$ together with the atoms to which they are attached form a cycloalkyl, substituted cycloalkyl, cycloalkenyl, substituted cycloalkenyl, cycloheteroalkyl, substituted cycloheteroalkyl, cycloheteroalkenyl or substituted cycloheteroalkenyl ring; $R_{31}$ is —H or alkyl; provided that $R_7$ and $R_8$ are not both —H.

In some embodiments, $R_7$ and $R_8$ are independently —H, substituted alkyl, substituted alkenyl, substituted arylalkyl, substituted arylalkenyl, heteroalkyl, substituted heteroalkyl, heteroalkenyl, substituted heteroalkenyl, substituted heteroarylalkyl, substituted heteroarylalkenyl. In other embodiments, $R_7$ and $R_8$ are independently —H, substituted alkyl, substituted alkenyl, heteroalkyl, substituted heteroalkyl, heteroalkenyl or substituted heteroalkenyl. In still other embodiments, $R_7$ and $R_8$ are independently —H, substituted alkyl or substituted alkenyl. In still other embodiments, $R_7$ and $R_8$ are independently —H or —CHR$_{32}$CO$_2$R$_{33}$; $R_{32}$ is —H, alkyl, substituted alkyl, alkenyl, substituted alkenyl, aryl, substituted aryl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, heteroaryl or substituted heteroaryl; and $R_{33}$ is alkyl, substituted alkyl, alkenyl, substituted alkenyl, cycloalkyl, cycloalkenyl, cycloheteroalkyl, cycloheteroalkenyl or substituted cycloheteroalkenyl. In still other embodiments, $R_7$ and $R_8$ are independently —H or —CHR$_{32}$CO$_2$R$_{33}$; $R_{32}$ is —H, alkyl, substituted alkyl, alkenyl or substituted alkenyl; and $R_{33}$ is alkyl, alkenyl or arylalkenyl. In still other embodiments, $R_7$ and $R_8$ are independently —H, or

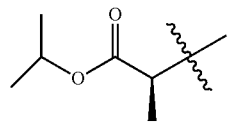

In still other embodiments, one of $R_7$ and $R_8$ are —H, and the other of $R_2$ and $R_3$ are

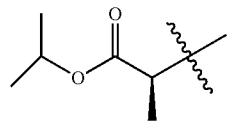

In some embodiments, $R_{15}$ is —H, alkyl, substituted alkyl, alkenyl, aryl, substituted aryl, arylalkyl, substituted arylalkyl, heteroaryl; and $R_{16}$, $R_{19}$, $R_{20}$, $R_{23}$, $R_{24}$, $R_{27}$, $R_{28}$ and $R_{31}$ are independently —H, alkyl, substituted alkyl, alkenyl, cycloalkyl, cycloalkenyl, cycloheteroalkyl, substituted cycloheteroalkyl, aryl, substituted aryl, arylalkyl, substituted arylalkyl, heteroalkyl, heteroalkenyl or heteroaryl; $R_{21}$ and $R_{22}$ are independently —H, alkyl, substituted alkyl, alkenyl, cycloalkyl, cycloalkenyl, cycloheteroalkyl, substituted cycloheteroalkyl, aryl, substituted aryl, arylalkyl, substituted arylalkyl, heteroalkyl, heteroalkenyl, heteroaryl or $R_{21}$ and $R_{22}$ together with the atoms to which they are attached form a cycloalkyl, substituted cycloalkyl, cycloalkenyl, substituted cycloalkenyl, cycloheteroalkyl, substituted cycloheteroalkyl, cycloheteroalkenyl or substituted cycloheteroalkenyl ring; $R_{25}$ and $R_{26}$ are independently —H, alkyl, substituted alkyl, alkenyl, cycloalkyl, cycloalkenyl, cycloheteroalkyl, substituted cycloheteroalkyl, aryl, substituted aryl, arylalkyl, substituted arylalkyl, heteroalkyl, heteroalkenyl, heteroaryl or $R_{25}$ and $R_{26}$ together with the atoms to which they are attached form a cycloalkyl, substituted cycloalkyl, cycloalkenyl, substituted cycloalkenyl, cycloheteroalkyl, substituted cycloheteroalkyl, cycloheteroalkenyl or substituted cycloheteroalkenyl ring; $R_{29}$ and $R_{30}$ are independently —H, alkyl, substituted alkyl, alkenyl, cycloalkyl, cycloalkenyl, cycloheteroalkyl, substituted cycloheteroalkyl, aryl, substituted aryl, arylalkyl, substituted arylalkyl, heteroalkyl, heteroalkenyl, heteroaryl or $R_{27}$ and $R_{28}$ together with the atoms to which they are attached form a cycloalkyl, substituted cycloalkyl, cycloalkenyl, substituted cycloalkenyl, cycloheteroalkyl, substituted cycloheteroalkyl, cycloheteroalkenyl or substituted cycloheteroalkenyl ring.

In some embodiments, B is —$NR_{15}$. In other embodiments, A is —$CHR_9$. In still other embodiments, Z is —H, —$CO_2R_{16}$ or —$CO_2NR_{17}R_{18}$. In still other embodiments, the compound of structural Formula (I) has the structure:

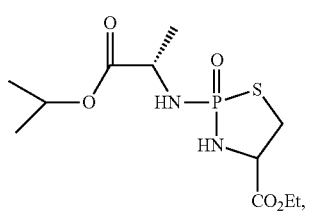

1

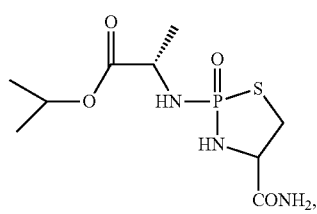

2

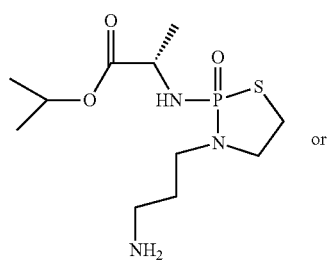

3 or

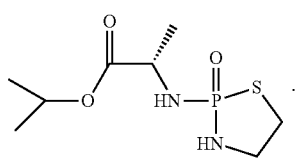

4

In some embodiments, B is —$NR_{15}$. In some embodiments, A is —$CHR_{12}CHR_{13}CHR_{14}$. In other embodiments, Z is —H. In still other embodiments, the compound of structural Formula (I) has the structure:

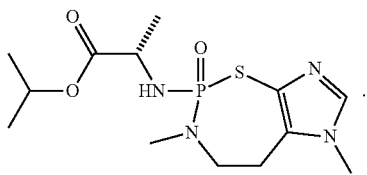

5

In some embodiments, B is —S—. In other embodiments, A is —$CHR_9$. In still other embodiments, Z is —$CO_2R_{16}$ or —$CH_2OR_{19}$. In still other embodiments, the compound of structural Formula (I) has the structure:

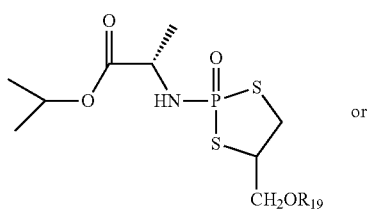

6 or

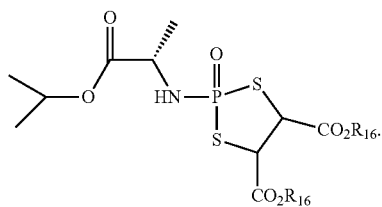

7

In some embodiments, B is —$CH_2NR_{31}$—. In other embodiments, A is —$CHR_9$. In still other embodiments, Z is H. In still other embodiments, the compound of structural Formula (I) has the structure:

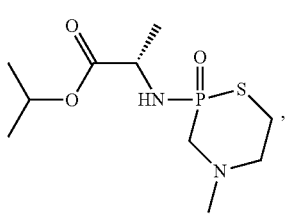

8

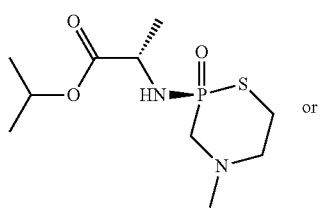

9 or

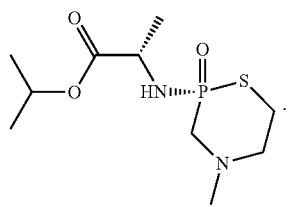

10

Compositions and Methods of Administration

The compositions provided herein contain therapeutically effective amounts of one or more of the compounds provided herein that are useful in the prevention, treatment, or amelioration of one or more of the symptoms of diseases or disorders described herein and a vehicle. Vehicles suitable for administration of the compounds provided herein include any such carriers known to those skilled in the art to be suitable for the particular mode of administration. In addition, the compounds may be formulated as the sole active ingredient in the composition or may be combined with other active ingredients.

The compositions contain one or more compounds provided herein. The compounds are, in some embodiments, formulated into suitable preparations such as solutions, suspensions, tablets, dispersible tablets, pills, capsules, powders, sustained release formulations or elixirs, for oral administration or in sterile solutions or suspensions for parenteral administration, as well as topical administration, transdermal administration and oral inhalation via nebulizers, pressurized metered dose inhalers and dry powder inhalers. In some embodiments, the compounds described above are formulated into compositions using techniques and procedures well known in the art (see, e.g., Ansel, Introduction to Pharmaceutical Dosage Forms, Seventh Edition (1999)).

In the compositions, effective concentrations of one or more compounds or derivatives thereof is (are) mixed with a suitable vehicle. The compounds may be derivatized as the corresponding salts, esters, enol ethers or esters, acetals, ketals, orthoesters, hemiacetals, hemiketals, acids, bases, solvates, ion-pairs, hydrates or prodrugs prior to formulation, as described above. The concentrations of the compounds in the compositions are effective for delivery of an amount, upon administration that treats, leads to prevention, or amelioration of one or more of the symptoms of diseases or disorders described herein. In some embodiments, the compositions are formulated for single dosage administration. To formulate a composition, the weight fraction of a compound is dissolved, suspended, dispersed or otherwise mixed in a selected vehicle at an effective concentration such that the treated condition is relieved, prevented, or one or more symptoms are ameliorated.

The active compound is included in the vehicle in an amount sufficient to exert a therapeutically useful effect in the absence of undesirable side effects on the patient treated. The therapeutically effective concentration may be predicted empirically by testing the compounds in in vitro and in vivo systems well known to those of skill in the art and then extrapolated therefrom for dosages for humans. Human doses are then typically fine-tuned in clinical trials and titrated to response.

The concentration of active compound in the composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of diseases or disorders as described herein.

In instances in which the compounds exhibit insufficient solubility, methods for solubilizing compounds may be used such as use of liposomes, prodrugs, complexation/chelation, nanoparticles, or emulsions or tertiary templating. Such methods are known to those of skill in this art, and include, but are not limited to, using co-solvents, such as dimethylsulfoxide (DMSO), using surfactants or surface modifiers, such as TWEEN®, complexing agents such as cyclodextrin or dissolution by enhanced ionization (i.e., dissolving in aqueous sodium bicarbonate). Derivatives of the compounds, such as prodrugs of the compounds may also be used in formulating effective compositions.

Upon mixing or addition of the compound(s), the resulting mixture may be a solution, suspension, emulsion or the like. The form of the resulting mixture depends upon a number of factors, including the intended mode of administration and the solubility of the compound in the selected vehicle. The effective concentration is sufficient for ameliorating the symptoms of the disease, disorder or condition treated and may be empirically determined.

The compositions are provided for administration to humans and animals in indication appropriate dosage forms, such as dry powder inhalers (DPIs), pressurized metered dose inhalers (pMDIs), nebulizers, tablets, capsules, pills, sublingual tapes/bioerodible strips, tablets or capsules, powders, granules, lozenges, lotions, salves, suppositories, fast melts, transdermal patches or other transdermal application devices/preparations, sterile parenteral solutions or suspensions, and oral solutions or suspensions, and oil-water emulsions containing suitable quantities of the compounds or derivatives thereof. The therapeutically active compounds and derivatives thereof are, in some embodiments, formulated and administered in unit-dosage forms or multiple-dosage forms. Unit-dose forms as used herein refer to physically discrete units suitable for human and animal subjects and packaged individually as is known in the art. Each unit-dose contains a predetermined quantity of the therapeutically active compound sufficient to produce the desired therapeutic effect, in association with the required vehicle. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid compositions can, for example, be prepared by dissolving, dispersing, or otherwise mixing an active compound as defined above and optional adjuvants in a vehicle, such as, for example, water, saline, aqueous dextrose, glycerol, glycols, ethanol, and the like, to thereby form a solution or suspension, colloidal dispersion, emulsion or liposomal formulation. If desired, the composition to be administered may also contain minor amounts of nontoxic auxiliary substances such as wetting agents, emulsifying agents, solubilizing agents, pH buffering agents and the like, for example, acetate, sodium citrate, cyclodextrin derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences, Mack Publishing Company, Easton, Pa., 15th Edition, 1975 or later editions thereof.

Dosage forms or compositions containing active ingredient in the range of 0.005% to 100% with the balance made up from vehicle or carrier may be prepared. Methods for preparation of these compositions are known to those skilled in the art. The contemplated compositions may contain 0.001%-100% active ingredient, in one embodiment 0.1-95%, in another embodiment 0.4-10%.

In certain embodiments, the compositions are lactose-free compositions containing excipients that are well known in the art and are listed, for example, in the U.S. Pharmacopeia (USP) 25-NF20 (2002). In general, lactose-free compositions contain active ingredients, a binder/filler, and a lubricant in compatible amounts. Particular lactose-free dosage forms contain active ingredients, microcrystalline cellulose, pre-gelatinized starch, and magnesium stearate.

Further provided are anhydrous compositions and dosage forms comprising active ingredients, since water can facilitate the degradation of some compounds. For example, the addition of water (e.g., 5%) is widely accepted as a means of simulating long-term storage in order to determine characteristics such as shelf-life or the stability of formulations over time. See, e.g., Jens T. Carstensen, *Drug Stability: Principles & Practice*, 2d. Ed., Marcel Dekker, NY, NY, 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous compositions and dosage forms provided herein can be prepared using anhydrous or low moisture containing ingredients and low moisture or low humidity conditions.

An anhydrous composition should be prepared and stored such that its anhydrous nature is maintained. Accordingly, anhydrous compositions are generally packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Oral dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms such as for example, capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an enteric coating; a film coating agent and modified release agent. Examples of binders include microcrystalline cellulose, methyl paraben, polyalkyleneoxides, gum tragacanth, glucose solution, acacia mucilage, gelatin solution, molasses, polyvinylpyrrolidine, povidone, crospovidones, sucrose and starch and starch derivatives. Lubricants include talc, starch, magnesium/calcium stearate, lycopodium and stearic acid. Diluents include, for example, lactose, sucrose, trehalose, lysine, leucine, lecithin, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water-soluble FD and C dyes, mixtures thereof; and water insoluble FD and C dyes suspended on alumina hydrate and advanced coloring or anti-forgery color/opalescent additives known to those skilled in the art. Sweetening agents include sucrose, lactose, mannitol and artificial sweetening agents such as saccharin and any number of spray dried flavors. Flavoring agents include natural flavors extracted from plants such as fruits and synthetic blends of compounds which produce a pleasant sensation or mask unpleasant taste, such as, but not limited to peppermint and methyl salicylate. Wetting agents include propylene glycol monostearate, sorbitan monooleate, diethylene glycol monolaurate and polyoxyethylene lauryl ether. Enteric-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate. Modified release agents include polymers such as the Eudragit® series and cellulose esters.

The compound, or derivative thereof, can be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, $H_2$ blockers, and diuretics. The active ingredient is a compound or derivative thereof as described herein. Higher concentrations, up to about 98% by weight of the active ingredient may be included.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Vehicles used in elixirs include solvents. Syrups are concentrated aqueous solutions of a sugar, for example, sucrose, and may contain a preservative. An emulsion is a two-phase system in which one liquid is dispersed in the form of small globules throughout another liquid. Carriers used in emulsions are non-aqueous liquids, emulsifying agents and preservatives. Suspensions use suspending agents and preservatives. Acceptable substances used in non-effervescent granules, to be reconstituted into a liquid oral dosage form, include diluents, sweeteners and wetting agents. Acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water-soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example, propylene carbonate, vegetable oils or triglycerides, is in some embodiments encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a liquid vehicle, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. RE28,819 and 4,358,603. Briefly, such formulations include, but are not limited to, those containing a compound provided herein, a dialkylated mono- or polyalkylene glycol, including, but not limited to, 1,2-dimethoxyethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including an acetal. Alcohols used in these formulations are any water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

Parenteral administration, in some embodiments characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Vehicles used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride.

Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcellulose, hydroxypropyl methylcellulose and polyvinylpyrrolidone. Emulsifying agents include Polysorbate 80 (Tween® 80). A sequestering or chelating agent of metal ions includes EDTA. Carriers also include ethyl alcohol, polyethylene glycol and propylene glycol for water miscible vehicles; and sodium hydroxide, hydrochloric acid, citric acid or lactic acid for pH adjustment.

The concentration of compound is adjusted so that an injection provides an effective amount to produce the desired pharmacological effect. The exact dose depends on the age, weight, body surface area and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In some embodiments, a therapeutically effective dosage is formulated to contain a concentration of at least about 0.01% w/w up to about 90% w/w or more, in certain embodiments more than 0.1% w/w of the active compound to the treated tissue(s).

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

Active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,639,480; 5,733,566; 5,739,108; 5,891,474; 5,922,356; 5,972,891; 5,980,945; 6,045,830; 6,087,324; 6,113,943; 6,197,350; 6,248,363; 6,264,970; 6,267,981; 6,376,461; 6,419,961; 6,589,548; 6,613,358; 6,699,500 and 6,740,634. Such dosage forms can be used to provide slow or controlled-release of one or more active ingredients using, for example, hydroxypropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients provided herein.

All controlled-release products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

In certain embodiments, the agent may be administered using intravenous infusion, an implantable osmotic pump, a transdermal patch, liposomes, or other modes of administration. In some embodiments, a pump may be used (see, Sefton, *CRC Crit. Ref. Biomed. Eng.* 14:201 (1987); Buchwald et al., *Surgery* 88:507 (1980); Saudek et al., *N. Engl. J. Med.* 321:574 (1989)). In other embodiments, polymeric materials can be used. In other embodiments, a controlled release system can be placed in proximity of the therapeutic target, i.e., thus requiring only a fraction of the systemic dose (see, e.g., Goodson, *Medical Applications of Controlled Release*, vol. 2, pp. 115-138 (1984)). In some embodiments, a controlled release device is introduced into a subject in proximity of the site of inappropriate immune activation or a tumor. Other controlled release systems are discussed in the review by Langer (*Science* 249:1527-1533 (1990)). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient contained in such parenteral compositions is highly dependent on the specific nature thereof, as well as the needs of the subject.

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a derivative thereof, in a suitable solvent. The solvent may contain an excipient which improves the stability or other pharmacological component of the powder or reconstituted solution, prepared from the powder. Excipients that may be used include, but are not limited to, an antioxidant, a buffer and a bulking agent. In some embodiments, the excipient is selected from dextrose, sorbitol, fructose, corn syrup, xylitol, glycerin, glucose, sucrose and other suitable agent. The solvent may contain a buffer, such as citrate, sodium or potassium phosphate or other such buffer known to those of skill in the art at, at about neutral pH. Subsequent sterile filtration of the solution followed by lyophilization under standard conditions known to those of skill in the art provides the desired formulation. In some embodiments, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carriers. The precise amount depends upon the selected compound. Such amount can be empirically determined.

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will, in some embodiments, have mass median geometric diameters of less than 5 microns, in other embodiments less than 10 microns.

Oral inhalation formulations of the compounds or derivatives suitable for inhalation include metered dose inhalers, dry powder inhalers and liquid preparations for administration from a nebulizer or metered dose liquid dispensing system. For both metered dose inhalers and dry powder inhalers, a crystalline form of the compounds or derivatives is the preferred physical form of the drug to confer longer product stability.

In addition to particle size reduction methods known to those skilled in the art, crystalline particles of the compounds or derivatives can be generated using supercritical fluid processing which offers significant advantages in the production of such particles for inhalation delivery by producing respirable particles of the desired size in a single step. (e.g., International Publication No. WO2005/025506). A controlled particle size for the microcrystals can be selected to ensure that a significant fraction of the compounds or derivatives is deposited in the lung. In some embodiments, these particles have a mass median aerodynamic diameter of about 0.1 to about 10 microns, in other embodiments, about 1 to about 5 microns and still other embodiments, about 1.2 to about 3 microns.

Inert and non-flammable HFA propellants are selected from HFA 134a (1,1,1,2-tetrafluoroethane) and HFA 227e (1,1,1,2,3,3,3-heptafluoropropane) and provided either alone or as a ratio to match the density of crystal particles of the compounds or derivatives. A ratio is also selected to ensure that the product suspension avoids detrimental sedimentation or cream (which can precipitate irreversible agglomeration) and instead promote a loosely flocculated system, which is easily dispersed when shaken. Loosely fluctuated systems are well regarded to provide optimal stability for pMDI canisters. As a result of the formulation's properties, the formulation contained no ethanol and no surfactants/stabilizing agents.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other excipients can also be administered.

For nasal administration, the preparation may contain an esterified phosphonate compound dissolved or suspended in a liquid carrier, in particular, an aqueous carrier, for aerosol application. The carrier may contain solubilizing or suspending agents such as propylene glycol, surfactants, absorption enhancers such as lecithin or cyclodextrin, or preservatives.

Solutions, particularly those intended for ophthalmic use, may be formulated as 0.01%-10% isotonic solutions, pH about 5-7.4, with appropriate salts.

Other routes of administration, such as transdermal patches, including iontophoretic and electrophoretic devices, and rectal administration, are also contemplated herein.

Transdermal patches, including iontophoretic and electrophoretic devices, are well known to those of skill in the art. For example, such patches are disclosed in U.S. Pat. Nos. 6,267,983, 6,261,595, 6,256,533, 6,167,301, 6,024,975, 6,010,715, 5,985,317, 5,983,134, and 5,860,957.

For example, dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm. Tablets and capsules for rectal administration are manufactured using the same substance and by the same methods as for formulations for oral administration.

The compounds provided herein, or derivatives thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,972,366, 5,900,252, 5,840,674, 5,759,542 and 5,709,874.

In some embodiments, liposomal suspensions, including tissue-targeted liposomes, such as tumor-targeted liposomes, may also be suitable as carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down phosphatidyl choline and phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The compounds or derivatives may be packaged as articles of manufacture containing packaging material, a compound or derivative thereof provided herein, which is effective for treatment, prevention or amelioration of one or more symptoms of the diseases or disorders, supra, within the packaging material, and a label that indicates that the compound or composition or derivative thereof, is used for the treatment, prevention or amelioration of one or more symptoms of the diseases or disorders, supra.

The articles of manufacture provided herein contain packaging materials. Packaging materials for use in packaging products are well known to those of skill in the art. See, e.g., U.S. Pat. Nos. 5,323,907, 5,052,558 and 5,033,252. Examples of packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease or disorder described herein.

Dosages

For use to treat or prevent infectious disease, the compounds described herein, or pharmaceutical compositions thereof, are administered or applied in a therapeutically effective amount. In human therapeutics, the physician will determine the dosage regimen that is most appropriate according to a preventive or curative treatment and according to the age, weight, stage of the disease and other factors specific to the subject to be treated. The amount of active ingredient in the formulations provided herein, which will be effective in the prevention or treatment of an infectious disease will vary with the nature and severity of the disease or condition, and the route by which the active ingredient is administered. The frequency and dosage will also vary according to factors specific for each subject depending on the specific therapy (e.g., therapeutic or prophylactic agents) administered, the severity of the infection, the route of administration, as well as age, body, weight, response, and the past medical history of the subject.

Exemplary doses of a formulation include milligram or microgram amounts of the active compound per kilogram of subject (e.g., from about 1 microgram per kilogram to about 50 milligrams per kilogram, from about 10 micrograms per kilogram to about 30 milligrams per kilogram, from about 100 micrograms per kilogram to about 10 milligrams per kilogram, or from about 100 micrograms per kilogram to about 5 milligrams per kilogram).

In some embodiments, a therapeutically effective dosage should produce a serum concentration of active ingredient of from about 0.001 ng/ml to about 50-200 µg/ml. The compositions, in other embodiments, should provide a dosage of from about 0.0001 mg to about 70 mg of compound per kilogram of body weight per day. Dosage unit forms are prepared to provide from about 0.01 mg, 0.1 mg or 1 mg to about 500 mg, 1000 mg or 5000 mg, and in some embodiments from about 10 mg to about 500 mg of the active ingredient or a combination of essential ingredients per dosage unit form.

The active ingredient may be administered at once or may be divided into a number of smaller doses to be administered at intervals of time. It is understood that the precise dosage and duration of treatment is a function of the disease being treated and may be determined empirically using known testing protocols or by extrapolation from in vivo or in vitro test data or subsequent clinical testing. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions and that the concentration ranges set forth herein are exemplary only and are not intended to limit the scope or practice of the claimed compositions.

It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with subject response.

For systemic administration, a therapeutically effective dose can be estimated initially from in vitro assays. For example, a dose can be formulated in animal models to achieve a circulating concentration range that includes the $IC_{50}$ as determined in cell culture (i.e., the concentration of test compound that is lethal to 50% of a cell culture), or the $IC_{100}$ as determined in cell culture (i.e., the concentration of compound that is lethal to 100% of a cell culture). Such information can be used to more accurately determine useful doses in humans.

Initial dosages can also be estimated from in vivo data (e.g., animal models) using techniques that are well known in the art. One of ordinary skill in the art can readily optimize administration to humans based on animal data.

Alternatively, initial dosages can be determined from the dosages administered of known agents by comparing the $IC_{50}$, MIC and/or $IC_{100}$ of the specific compound disclosed herein with that of a known agent and adjusting the initial dosages accordingly. The optimal dosage may be obtained from these initial values by routine optimization In cases of local administration or selective uptake, the effective local concentration compound used may not be related to plasma concentration. One of skill in the art will be able to optimize therapeutically effective local dosages without undue experimentation.

Ideally, a therapeutically effective dose of the compounds described herein will provide therapeutic benefit without causing substantial toxicity. Toxicity of compounds can be determined using standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds which exhibit high therapeutic indices are preferred. The data obtained from these cell culture assays and animal studies can be used in formulating a dosage range that is not toxic for use in subjects. The dosage of the compounds described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition (See, e.g., Fingl et al., 1975, *In: The Pharmacological Basis of Therapeutics*, Ch.1, p. 1).

The therapy may be repeated intermittently. In certain embodiments, administration of the same formulation provided herein may be repeated and the administrations may be separated by at least 1 day, 2 days, 3 days, 5 days, 10 days, 15 days, 30 days, 45 days, 2 months, 75 days, 3 months, or 6 months.

Methods of Use of the Compounds and Compositions

Methods of treating, preventing, or ameliorating symptoms of medical disorders such as, for example, cystinuria, cystinosis, cancer, neurodegenerative disease, Parkinson's disease, Huntington's disease, malaria, nonalcoholic fatty liver disease, radiation poisoning, arsenic poisoning, Wilson's disease or rheumatoid arthritis with the disclosed compounds and pharmaceutical compositions are described herein. In practicing the methods, therapeutically effective amounts of the compounds or compositions, described herein, supra, are administered to the patient with the disorder or condition.

Combination Therapy

The compounds and compositions disclosed herein may also be used in combination with one or more other active ingredients. In certain embodiments, the compounds may be administered in combination, or sequentially, with another therapeutic agent. Such other therapeutic agents include those known for treatment, prevention, or amelioration of one or more symptoms associated with cystinuria, cystinosis, cancer, neurodegenerative disease, Parkinson's disease, Huntington's disease, malaria, nonalcoholic fatty liver disease, radiation poisoning, arsenic poisoning, Wilson's disease or rheumatoid arthritis.

It should be understood that any suitable combination of the compounds and compositions provided herein with one or more of the above therapeutic agents and optionally one or more further pharmacologically active substances are considered to be within the scope of the present disclosure. In some embodiments, the compounds and compositions provided herein are administered prior to or subsequent to the one or more additional active ingredients.

Finally, it should be noted that there are alternative ways of implementing the present invention. Accordingly, the present embodiments are to be considered as illustrative and not restrictive, and the invention is not to be limited to the details given herein but may be modified within the scope and equivalents of the appended claims.

All publications and patents cited herein are incorporated by reference in their entirety.

The following examples are provided for illustrative purposes only and are not intended to limit the scope of the invention.

EXAMPLES

Isopropyl (bis((2-((tert-butoxycarbonyl)amino)ethyl)thio)phosphoryl)-L-alaninate (101)

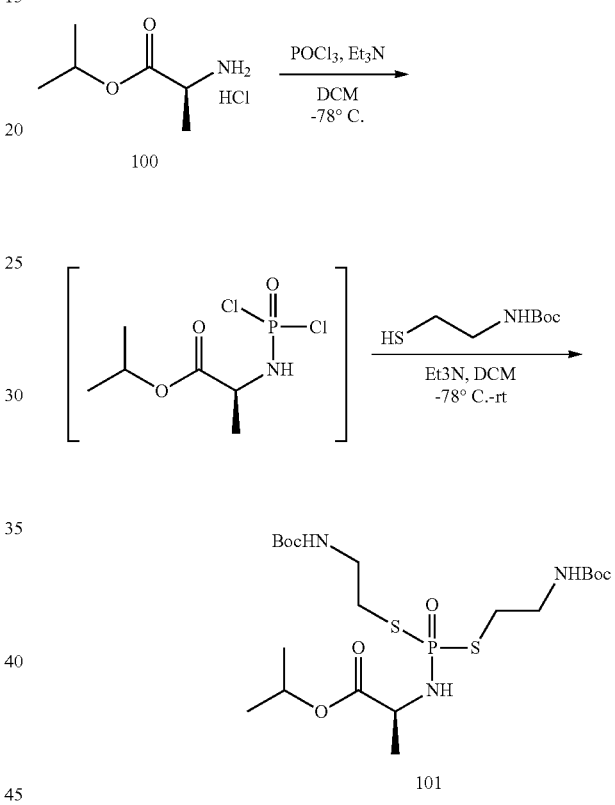

To a stirred solution of L-Alanine isopropyl ester hydrochloride (100) (1.0 gm, 5.96 mmol) in DCM (30.0 ml), was added POCl$_3$ (0.557 ml, 5.96 mmol) at 25-30° C. and the reaction mixture was stirred at 25° C. for 30 min. Then the reaction mixture was cooled to −78° C. and triethylamine (1.66 ml, 11.857 mmol) was added dropwise over 20 minutes. After addition was complete the reaction mixture was stirred at −78° C. for additional 1 hour. Then N-Boc cysteamine (2.11 gm, 11.9 mmol) and triethylamine (1.66 ml, 11.857 mmol) were added successively. After addition was complete, the temperature of the reaction mixture was raised gradually to 25° C. and stirring was continued for 24 h. Water was added and the reaction mixture was extracted with DCM (100 ml, 2×). The combined organic extracts were dried over anhydrous Na$_2$SO$_4$ and concentrated under vacuum to afford the crude compound as a pale-yellow liquid. The crude compound was purified over silica gel (100-200 mesh, 40% ethyl acetate/n-hexane) to provide the pure compound 101 (1.5 g, crude) as a gummy liquid. LC-MS: 530.35 [M+H]$^+$.

Example 1: Isopropyl (2-oxido-1,3,2-thiazaphospholidin-2-yl)-L-alaninate (4)

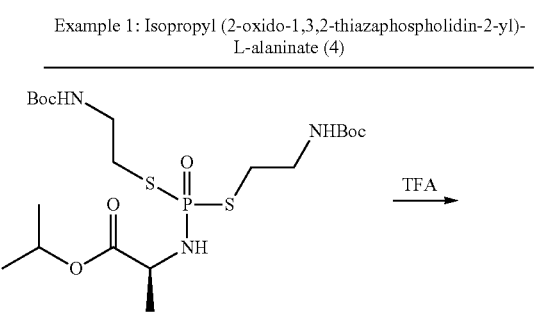

To a stirred solution of compound 101 (1.0 gm, 2.242 mmol) in DCM (20 ml) was added trifluoroacetic acid (0.72 ml, 18.8 mmol) dropwise at 0° C., the reaction mixture was allowed to warm to 25° C., stirred for 16 h and the solvent removed to provide the crude compound as a thick gummy liquid. The crude was purified by using reverse phase prep HPLC and lyophilized to provide compound 21 (0.104 g, 12%) as white solid. $^1$H-NMR (400 MHz, DMSO-$d_6$): δ 1.17-1.30 (m, 9H), 2.97-3.21 (m, 3H), 3.62-3.70 (m, 1H), 4.85-4.92 (m, 1H), 5.18-5.0 (m, 1H). LC-MS: 271.14 [M+H$^+$].

Scheme 1 illustrates the preparation of compounds 8, 9 and 10.

Scheme 1

Isopropyl (((2-((tert-butoxycarbonyl)(methyl)amino)ethyl)thio)((tosyloxy)methyl)phosphoryl)-L-alaninate (103)

To a stirred solution of (dichlorophosphoryl)methyl 4-methylbenzenesulfonate (2.5 g, 8.2 mmol) in dichloromethane (50 mL) at −78° C. was added L-Alanine isopropyl ester hydrochloride 102 (1.38 g, 8.2 mmol) dropwise (~30 min) and stirred for 10 min. Then triethylamine (2.3 mL, 16.5 mmol) was added to the reaction mixture. The resulting reaction mixture was stirred for another 1 h at −78° C. Then, the above reaction mixture was allowed to warm to 0° C. and a solution of tert-butyl (2-mercaptoethyl)(methyl)carbamate (1.6 g, 8.2 mmol) in dichloromethane (50 mL) and triethylamine (2.3 mL, 16.5 mmol) were added to the reaction mixture. The resulting reaction mixture was allowed to warm to room temperature and stirred overnight. After completion of the addition, the reaction mixture was cool to 0° C. and quenched with ice-cold water (50 mL) and extracted with ethyl acetate (2×100 mL). The combined organic layers were dried over anhydrous $Na_2SO_4$ and concentrated under reduced pressure at 30° C. to afford a gummy liquid. The crude compound was purified using silica gel (100-200 mesh) column chromatography by using 0-80% ethyl acetate in n-hexane as an eluent to afford isopropyl (((2-((tert-butoxycarbonyl)(methyl)amino)ethyl)thio)((tosyloxy)methyl)phosphoryl)-L-alaninate 103 (1.2 g, 26%) as an pale-yellow gummy liquid. $^1$H-NMR (400 MHz, CDCl$_3$) δ: 7.82 (d, J=8.4 Hz, 2H), 7.38-7.36 (m, 2H), 5.06-5.01 (m, 1H), 4.30-4.22 (m, 2H), 4.06-4.04 (m, 1H), 3.60-3.38 (m, 2H), 3.09-2.91 (m, 2H), 2.86 (s, 3H), 2.46 (s, 3H), 1.48-1.40 (m, 12H), 1.28-1.24 (m, 6H); LCMS: 94.19%, m/z 553.3 [M+H]$^+$.

Example 2: Isopropyl (4-methyl-2-oxido-1,4,2-thiazaphosphinan-2-yl)-L-alaninate (8)

To a stirred solution of Isopropyl (((2-((tert-butoxycarbonyl)(methyl)amino)ethyl)thio)((tosyloxy)methyl)phosphoryl)-L-alaninate 103 (4.2 g, 7.6 mmol) in CH$_2$Cl$_2$ (45 mL) was added by trifluoroacetic acid (2.95 mL, 3.80 mmol) dropwise at 0° C. After addition was complete, the resulting reaction mixture was stirred at room temperature for 16 h. After completion of the reaction (monitored by TLC) the reaction mixture was concentrated under reduced pressure at 35° C. to provide the crude compound as a thick gummy liquid. Then the crude compound was dissolved in ice cold H$_2$O and cooled to 0° C. and treated with aq. NaHCO$_3$ and extracted with 10% methanol in DCM (50 mL×3). The combined organic layer was dried over Na$_2$SO$_4$ and concentrated under vacuum to obtained crude product. The crude compound was purified by prep-HPLC afford 400 mg of 8 as a mixture of diastereomers (92%:7%, by chiral SFC). $^1$H-NMR (400 MHz, DMSO-d$_6$) δ: 5.46 (dd, J=10.4, 14.4 Hz, 1H), 4.95-4.87 (m, 1H), 3.87-3.80 (m, 1H), 3.05-2.84 (m, 4H), 2.50-2.47 (m, 1H), 2.37-2.28 (m, 4H), 1.32-1.29 (m, 3H), 1.25-1.19 (m, 6H); HPLC: 98.1%; LCMS: 97.94%, m/z 281.37 [M+H]$^+$.

Example 3: Isopropyl ((S)-4-methyl-2-oxido-1,4,2-thiazaphosphinan-2-yl)-L-alaninate (9) and Isopropyl ((R)-4-methyl-2-oxido-1,4,2-thiazaphosphinan-2-yl)-L-alaninate (10)

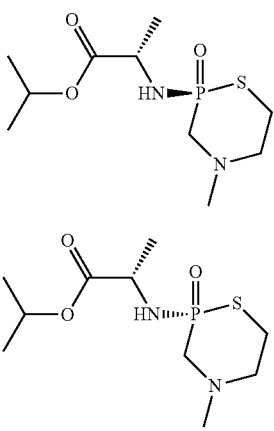

9

10

Compound 8 (mixture of diastereomers) was separated by chiral SFC (Chiralpak IC (250×4.6×5µ, % CO$_2$:85%, % co Solvent: 15% (100% Methanol), Total Flow: 3.0 g/min, back pressure:100 bar, Temperature: 30° C., Wavelength: 205 nm) to afford 9 (Peak-1) and 10 (Peak-2).

Isopropyl ((S)-4-methyl-2-oxido-1,4,2-thiazaphosphinan-2-yl)-L-alaninate (9). $^1$H-NMR (400 MHz, DMSO-d$_6$) δ: 5.45 (dd, J=10.0, 14.4 Hz, 1H), 4.95-4.88 (m, 1H), 3.85-3.80 (m, 1H), 3.06-2.83 (m, 4H), 2.50-2.47 (m, 1H), 2.37-2.29 (m, 4H), 1.30 (d, J=7.2 Hz, 3H), 1.22-1.17 (m, 6H); HPLC purity: 98.27%; LC-MS: 96.4%, m/z 281.07 [M+H]$^+$; Chiral purity: 97.24 (by chiral SFC).

Isopropyl ((R)-4-methyl-2-oxido-1,4,2-thiazaphosphinan-2-yl)-L-alaninate (10). $^1$H-NMR (400 MHz, DMSO-d$_6$) δ: 5.45 (dd, J=10.4, 14.4 Hz, 1H), 4.92-4.86 (m, 1H), 3.92-3.85 (m, 1H), 3.00-2.93 (m, 3H), 2.77-2.72 (m, 1H), 2.63-2.56 (m, 1H), 2.50-2.43 (m, 1H), 2.28 (d, J=2.4 Hz, 3H), 1.31 (d, J=7.2 Hz, 3H), 1.23-1.17 (m, 6H); HPLC purity: 99.45%; LCMS: 99.26%, m/z 281.29 [M+H]$^+$, Chiral purity: 93.84% (By chiral SFC).

What is claimed is:

1. A compound having the structure:

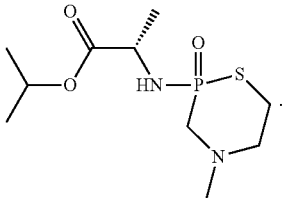 [SMILES: CC(C)OC(=O)[C@H](C)NP1(=O)CN(C)CCS1]

2. A pharmaceutical composition comprising the compound of claim 1 and a pharmaceutically acceptable vehicle.

3. A compound having the structure:

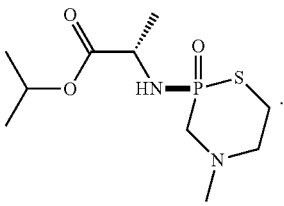 [SMILES: CC(C)OC(=O)[C@H](C)N[P@]1(=O)CN(C)CCS1 ; "."]

4. A pharmaceutical composition comprising the compound of claim 3 and a pharmaceutically acceptable vehicle.

5. A compound having the structure:

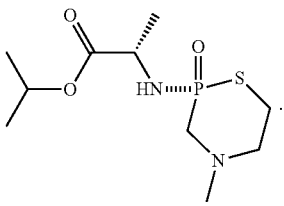 [SMILES: CC(C)OC(=O)[C@H](C)N[P@@]1(=O)CN(C)CCS1]

6. A pharmaceutical composition comprising the compound of claim 5 and a pharmaceutically acceptable vehicle.

* * * * *